US00PP19586P2

(12) United States Plant Patent
van Kleinwee

(10) Patent No.: US PP19,586 P2
(45) Date of Patent: Dec. 23, 2008

(54) *PETUNIA* PLANT NAMED 'PETOUCH'

(50) Latin Name: *Petunia hybrida*
Varietal Denomination: Petouch

(75) Inventor: Theodorus Cornelis Maria van Kleinwee, Hoorn (NL)

(73) Assignee: Syngenta Seeds B.V., Enkhuizen (NL)

( * ) Notice: Subject to any disclaimer, the term of this patent is extended or adjusted under 35 U.S.C. 154(b) by 0 days.

(21) Appl. No.: 12/009,106

(22) Filed: Jan. 16, 2008

(51) Int. Cl.
*A01H 5/00* (2006.01)

(52) U.S. Cl. ..... Plt./356
(58) Field of Classification Search ..... Plt./356
See application file for complete search history.

*Primary Examiner*—Annette H Para
(74) *Attorney, Agent, or Firm*—S. Matthew Edwards

(57) ABSTRACT

A new and distinct cultivar of *Petunia* plant named 'Petouch' characterized by its trailing, outwardly spreading plant habit, freely branching habit, freely flowering habit, single flowers that are white-violet in color, and good garden performance.

1 Drawing Sheet

Latin name of the genus and species of the plant claimed: *Petunia hybrida.*
Varietal denomination: 'Petouch'.

BACKGROUND OF THE NEW PLANT

The present invention relates to a new and distinct cultivar of *Petunia* plant, botanically known as *Petunia hybrida,* and hereinafter referred to by the cultivar name 'Petouch.'

The new *Petunia* is a product of a planned breeding program conducted in Enkhuizen, Netherlands. The new *Petunia* cultivar is freely flowering with a trailing and spreading plant habit and an attractive leaf and flower coloration.

The new *Petunia* originated from a cross between female parent 'Y0892,' an early and blue flowering unnamed seedling of own breeding, and male parent 'A1057,' a very good branching and rather late selection of own breeding.

Asexual reproduction of the new cultivar by terminal cuttings at Enkhuizen since August 2002, has shown that the unique features of this new *Petunia* are stable and reproduced true to type in successive generations.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new *Petunia.*

SUMMARY OF THE INVENTION

The following traits have been repeatedly observed and are determined to be the unique characteristics of 'Petouch.' These characteristics in combination distinguish 'Petouch' as a new and distinct cultivar:

1. Spreading plant habit
2. Freely branching
3. Freely flowering

4. White-violet flower color
5. Good outdoor performance

In side-by-side comparisons conducted in Enkhuizen, Netherlands, plants of the new *Petunia* differed from plants of the female parent selection in the following characteristics:

1. Plants of the new *Petunia* flower later than plants of the female parent selection
2. Plants of the new *Petunia* are less violet than plants of the female parent selection.

In side-by-side comparisons conducted in Enkhuizen, Netherlands, plants of the new *Petunia* differed from plants of the male parent selection in the following characteristics:

1. Plants of the new *Petunia* are more branched than plants of the male parent selection.
2. Plants of the new *Petunia* flower earlier than plants of the male parent selection.

TABLE 1

DIFFERENCES BETWEEN THE NEW CULTIVAR 'PETOUCH' AND A SIMILAR CULTIVAR

| | 'Petouch' | 'Petwiblvgr' (U.S. Plant Patent No. 17,260) |
|---|---|---|
| Petal visibility of vein pattern | Less clearly | More clearly |
| Vigour | Less vigorous | More vigorous |
| Earliness of flowering | 6 weeks after planting | 7 weeks after planting |

DESCRIPTION OF THE NEW CULTIVAR

The observations and measurements describe plants grown in Enkhuizen, Netherlands, practice circumstances indoor in hanging baskets of diameter 25 cm during the early spring with day temperatures ranging from 15 to 20° C., night temperatures ranging from 5 to 15° C. Plants used for the photographs and description were about 25 weeks from planting rooted cuttings.

In the following description, color references are made to The Royal Horticultural Society Colour Chart, 2001 Edition, except where general terms of ordinary dictionary significance are used.

The plant:

*Classification.*—Botanical: *Petunia hybrida.*

Parentage:

*Female parent.*—Proprietary selection Y0892, not patented.

*Male parent.*—Proprietary selection A1057, not patented.

Propagation:

*Type.*—Terminal cuttings.

*Time to initiate roots.*—7 days.

*Time to develop roots.*—14 days.

*Root description.*—Fine, fibrous, white in color

*Rooting habit.*—Freely branching.

Plant description:

*Form.*—Annual flowering plant; indeterminate; initially upright, later on trailing and outwardly spreading. Freely branching habit; about eight basal branches each with five to seven lateral branches. Pinching enhances development of lateral branches.

*Usage.*—Appropriate for hanging baskets, window boxes, patio containers and landscape applications.

*Plant height* (*from soil level to top of plant plane*).—About 20 cm.

*Plant diameter* (*area of spread*).—About 60 cm.

*Vigor.*—Vigorous; rapid growth rate.

*Lateral branches.*—Length: About 40 cm. Diameter: About 3 mm. Internode length: 1.5–2.5 cm. Texture: Canescent. Color: 144B.

The foliage:

*Arrangement.*—Opposite, decussate, sessile, simple.

*Length.*—2–3.5 cm.

*Width.*—1.5–2 cm.

*Shape.*—Lanceolate.

*Apex.*—Acuminate.

*Base.*—Attenuate.

*Margin.*—Entire, slightly ciliated.

*Texture, upper and lower surfaces.*—Sparsely pubescent.

*Venation.*—Pinnate.

*Color.*—Developing foliage, upper and lower surfaces: 147A to 147B. Fully expanded foliage, Upper surface: 147A. Venation upper surface: 143B to 143C. Lower surface: 147B. Venation lower surface: 143B.

*Petiole.*—Length: About 3 mm. Diameter: About 3 mm. Color, upper and lower surface: 143B. Texture: Sparsely pubescent.

The flower:

*Flower type and habit.*—Single funnel-shaped flowers, slightly rotate. Flowers face mostly upward and outward; axillary. Freely flowering habit, five to ten open flowers and about four flower buds per lateral branch at a time.

*Natural flowering season.*—Spring until frost in the autumn; flowering continuous.

*Flowers longevity on the plant.*—5 days.

*Fragrance.*—Strong.

*Flower size.*—Diameter: 5–6 cm. Tube length: About 3 cm. Throat diameter, distal end: About 1 cm. Tube diameter, proximal end: 2–3 mm.

*Flower buds.*—Length: 3–4 cm. Diameter: About 5 mm. Shape: Elongated oblong with ruffled apices. Color: N92A.

*Petals*—Quantity/arrangement: Five petals fused in a single whorl, funnel shaped, slightly rotate. Length from throat: 4–5 cm. Width: About 2.5 cm. Shape: Spatulate. Apex: Rounded. Margin: Entire. Texture, upper and lower surfaces: Smooth, velvety. Color When opening, upper surface: 155B, venation 150D. When opening, lower surface: 155C, venation 83B to 83C. Fully opened, upper surface: 155B, venation 150C. Fully opened, lower surface: 155C, venation 83C to 83D. Flower throat (inside): 150B, venation N92A. Flower tube (outside): N77D, venation 150C. Venation, throat: N92A. Venation, tube: 150C.

*Sepals.*—Arrangement/appearance: Single whorl of five sepals fused at base, rotate shape. Length: 1.5–2 cm. Width: About 1 cm. Shape: Ligulate. Apex: Rounded. Margin: Ciliated. Texture, upper and lower surfaces: Puberulous. Color, upper surface: 137A. Color, lower surface: 137C.

*Peduncles.*—Length: 1.5–2 cm. Width: About 1 mm. Angle: About 45° to 60° from the stem. Strength: Strong. Texture: Puberulous. Color: 144A.

Reproductive organs:

*Stamens, quantity per flower.*—Five.

*Anther shape.*—Two-parted, rounded, ends fused.

*Anther length.*—About 1 mm.

*Anther diameter.*—About 1 mm.

*Anther color.*—2D.

*Pollen amount.*—Much pollen.

*Pollen color.*—2D.

*Pistils, quantity per flower.*—One.

*Pistil length.*—About 2.2 cm.

*Style length.*—About 2.0 cm.

*Style color.*—150C.

*Stigma shape.*—Ovate.

*Stigma color.*—N144C.

*Ovary color.*—144C.

Seed development: Seed and/or fruit production has not been observed to date.

Disease and pest resistance: No disease/pest resistance has been observed to date.

Garden performance: Plants of the *Petunia* named 'Petouch' have been observed to have good garden performance. Plants of the *Petunia* named 'Petouch' have been noted to tolerate rain, wind and temperatures from 2 to 39° C.

What is claimed is:

1. A new and distinct cultivar of *Petunia* plant named 'Petouch', as substantially illustrated and described herein.

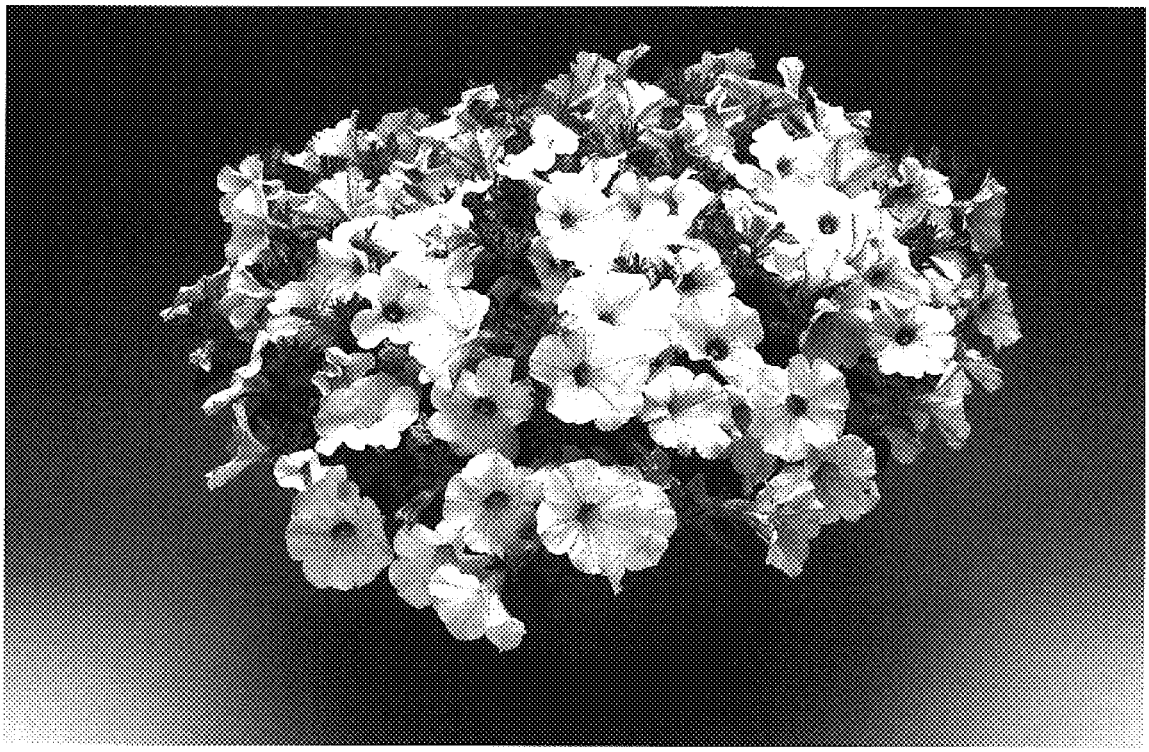

* * * * *